United States Patent
Dominguez-Manzanares

(10) Patent No.: US 8,097,652 B2
(45) Date of Patent: Jan. 17, 2012

(54) AMPA RECEPTOR POTENTIATORS

(75) Inventor: Esteban Dominguez-Manzanares, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 226 days.

(21) Appl. No.: 12/517,431

(22) PCT Filed: Dec. 6, 2007

(86) PCT No.: PCT/US2007/086567
§ 371 (c)(1),
(2), (4) Date: Jun. 3, 2009

(87) PCT Pub. No.: WO2008/073789
PCT Pub. Date: Jun. 19, 2008

(65) Prior Publication Data
US 2010/0010090 A1   Jan. 14, 2010

Related U.S. Application Data

(60) Provisional application No. 60/888,562, filed on Feb. 7, 2007.

(30) Foreign Application Priority Data

Dec. 11, 2006   (EP) .................................. 06380319

(51) Int. Cl.
A61K 31/192   (2006.01)
A61P 25/16    (2006.01)
A61P 25/24    (2006.01)

(52) U.S. Cl. .......................... 514/568; 514/605; 558/413
(58) Field of Classification Search ................. 514/605, 514/568; 558/413
See application file for complete search history.

(56) References Cited

U.S. PATENT DOCUMENTS
6,303,816 B1 * 10/2001 Arnold et al. .................. 564/82

FOREIGN PATENT DOCUMENTS
WO   WO 98/33496 A   8/1998
WO   WO01/90057 A    11/2001

OTHER PUBLICATIONS

Ornstein et al Biarylpropylsulfonamides as Novel, potent potentiators of 2-amino-3-(5-methyl-3-hydroxyisoxazol-4-yl)-propanoic acid (AMPA) receptors. J. Med. Chem. 2000, 43, pp. 4354-4358.*

* cited by examiner

*Primary Examiner* — Jennifer M Kim
(74) *Attorney, Agent, or Firm* — Tonya L. Combs

(57) ABSTRACT

The present invention relates to a compound of Formula (I) or a pharmaceutically acceptable salt thereof which is useful for the treatment of conditions associated with glutamate hypofunction, such as psychiatric and neurological disorders.

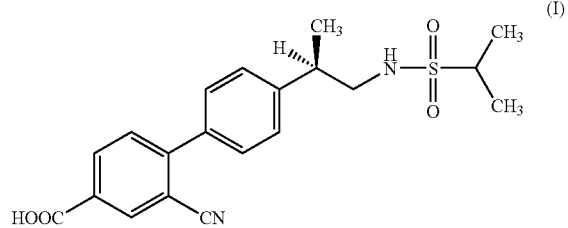

7 Claims, No Drawings

AMPA RECEPTOR POTENTIATORS

This is the national phase application, under 35 USC 371, for PCT/US2007/086567 filed 6 Dec. 2007 which claims the benefit, under 35 USC 119(e), of EP provisional application 06380319.1 filed 11 Dec. 2006 and U.S. provisional application 60/888,562 filed 7 Feb. 2007.

BACKGROUND OF THE INVENTION

Glutamate is the major excitatory neurotransmitter in the central nervous system. AMPA receptors are one of three glutamate receptor ion channel subtypes identified, based on its sensitivity to the selective activator, α-amino-3-hydroxy-5-methyl-4-isoxazole propionic acid (AMPA). AMPA receptors mediate cellular responses to glutamate by direct and indirect mechanisms. When activated by glutamate or AMPA, AMPA receptor ion channels allow sodium ($Na^+$) and calcium ions ($Ca^{2+}$) to pass directly through the channel pore.

Ion channel currents activated by glutamate via AMPA receptors are transient. The time course of currents is modified by refractory states caused during glutamate binding which is referred to as desensitization and by the rate of glutamate removal from the ion channel binding site which results in deactivation. Ion influx through AMPA receptors may be enhanced by compounds that either prevent desensitization or by compounds that slow deactivation rates. Compounds that enhance glutamate-stimulated ion influx at AMPA receptors are known as positive AMPA receptor allosteric modulators or AMPA receptor potentiators. Since AMPA receptors play a pivotal role in mediating fast excitatory transmission in the central nervous system, molecules that enhance AMPA receptor function have multiple therapeutic targets. Moreover, compounds that allosterically potentiate AMPA receptors have been shown to enhance synaptic activity in vitro and in vivo. Such compounds have also been shown to enhance learning and memory in rats, monkeys, and humans.

Several International Patent Application Publications, see WO 98/33496, WO 01/68592, and WO 01/90057, disclose certain sulfonamide derivatives useful, for example, as AMPA potentiators, and for treating a variety of disorders such as psychiatric and neurological disorders, and sexual dysfunction. There remains, however, a need for AMPA receptor potentiators that have increased potency and a greater margin of safety. The compounds of the Formula I may also be useful for improving memory (both short term and long term) and learning ability.

BRIEF SUMMARY OF THE INVENTION

The present invention provides a compound of Formula I:

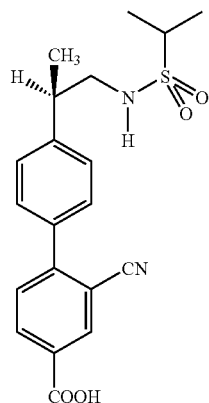

or a pharmaceutically acceptable salt thereof.

The present invention provides a compound of Formula I for use as a pharmaceutical. Moreover, the present invention provides a method of potentiating glutamate receptor function in a patient, which comprises administering to said patient in need of such treatment an effective amount of a compound of Formula I or a pharmaceutically acceptable salt thereof.

In addition, the present invention further provides a method of treating schizophrenia, cognitive deficits associated with schizophrenia, Alzheimer's disease, dementia of the Alzheimer's type, mild cognitive impairment, Parkinson's disease, or depression in a patient, which comprises administering to a patient in need of such treatment an effective amount of a compound of Formula I or a pharmaceutically acceptable salt thereof.

According to another aspect, the present invention provides the use of a compound of Formula I, or a pharmaceutically acceptable salt thereof, for the manufacture of a medicament for treating schizophrenia, cognitive deficits associated with schizophrenia, Alzheimer's disease, dementia of the Alzheimer's type, mild cognitive impairment, Parkinson's disease, or depression.

The invention further provides pharmaceutical compositions comprising, a compound of Formula I, or a pharmaceutically acceptable salt thereof, and a pharmaceutically acceptable carrier, diluent, or excipient.

DETAILED DESCRIPTION OF THE INVENTION

As used herein the term "potentiating glutamate receptor function" refers to any increased responsiveness of glutamate receptors, for example AMPA receptors, to glutamate or an agonist, and includes but is not limited to inhibition of rapid desensitization or deactivation of AMPA receptors to glutamate.

A wide variety of conditions may be treated or prevented by the compound of Formula I and pharmaceutically acceptable salts thereof through their action as potentiators of glutamate receptor function. See International Patent Applications WO 98/33496 and WO 01/68592, describing various disorders treated by potentiators of glutamate receptor function. Such conditions include those associated with glutamate hypofunction, such as psychiatric and neurological disorders, for example cognitive disorders and neuro-degenerative disorders such as Alzheimer's disease; dementia of the Alzheimer's type, age-related dementias; age-induced memory impairment; movement disorders such as tardive dyskinesia, Parkinson's disease; reversal of drug-induced states (such as cocaine, amphetamines, alcohol-induced states); depression; attention deficit disorder; attention deficit hyperactivity disorder; psychosis such as schizophrenia; cognitive deficits associated with psychosis such as schizophrenia, drug-induced psychosis, stroke, and sexual dysfunction. The present invention provides the use of a compound of Formula I for the treatment of each of these conditions, in addition to those disorders described in International Patent Applications WO 98/33496 and WO 01/68592. The compound of Formula I may also be useful for improving memory (both short term and long term) and learning ability.

It is understood by one of ordinary skill in the art that cognition includes various "domains". These domains include short-term memory, long term memory, working memory, executive function, and attention. As used herein the term "cognitive disorder" is meant to encompass any disorder characterized by a deficit in one or more of the cognitive domains, including but not limited to short term memory, long term memory, working memory, executive function, and attention. It is further understood that the term "cognitive disorder" includes, but is not limited to the following specific disorders: age-related cognitive decline, mild cognitive impairment, Alzheimer's disease, dementia, dementia of the Alzheimer's type, Parkinson's dementia, Lewy Body dementia, substance-induced persisting dementia, alcohol-induced persisting dementia, alcohol-induced cognitive impairment, AIDS-induced dementia, learning disorders, cognitive deficits subsequent to cardiac bypass surgery and grafting, stroke, cerebral ischemia, spinal cord trauma, head trauma, perinatal hypoxia, cardiac arrest, and hypoglycemic neuronal damage, vascular dementia, multi-infarct dementia, cognitive deficits associated with amylotrophic lateral sclerosis, and cognitive deficits associated with multiple sclerosis. Mild cognitive impairment has been defined as a potential prodromal phase of dementia associated with Alzheimer's disease based on clinical presentation and on progression of patients exhibiting mild cognitive impairment to Alzheimer's dementia over time. (Morris, et al., Arch. Neurol., 58, 397-405 (2001); Petersen, et al., Arch. Neurol., 56, 303-308 (1999)).

The fourth edition of the Diagnostic and Statistical Manual of Mental Disorders (DSM-IV) (1994, American Psychiatric Association, Washington, D.C.) provides a diagnostic tool for identifying many of the disorders described herein. The skilled artisan will recognize that there are alternative nomenclatures, nosologies, and classification systems for disorders described herein, including those as described in the International Statistical Classification of Diseases and Related Health Problems, tenth revision (ICD-10) (1992, World Health Organization, Geneva) and that terminology and classification systems evolve with medical scientific progress.

The present invention includes the pharmaceutically acceptable salts of the compound defined by Formula I. A compound of this invention possesses an acidic group, and accordingly reacts with any of a number of organic and inorganic bases to form a pharmaceutically acceptable salt. The term "pharmaceutically acceptable salt" as used herein, refers to salts of the compound of Formula I which are substantially non-toxic to living organisms. Such salts include the pharmaceutically acceptable salts listed in Journal of Pharmaceutical Science, 66, 2-19 (1977), which are known to the skilled artisan.

The compound of Formula I may be prepared, for example, following analogous procedures set forth in International Patent Application Number WO 98/33496. More specifically, the compound of Formula I can be prepared as set forth in the schemes, methods, and examples set forth below. The reagents and starting materials are readily available to the skilled artisan.

The abbreviations, symbols and terms used in the examples and assays have the following meanings: AcOH=acetic acid, DCM=dichloromethane, DMAP=dimethylaminopyridine, DME=dimethoxyethane, DMF=N,N-dimethylformamide, DMSO=dimethyl sulfoxide, (dppf)=1,1'-bis(diphenylphosphino)ferrocene, e.e.=enantiomeric excess, $Et_3N$=triethylamine, EtOAc=ethyl acetate, EtOH=ethanol, GC=Gas chromatography, 1H NMR=Proton nuclear magnetic resonance spectrometry, HPLC=high performance liquid chromatography, MS=Mass spectrometry, $Tf_2O$=triflic anhydride.

Preparations

Preparation 1

Ethyl 4-hydroxy-3-iodo-benzoate

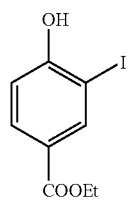

Dissolve ethyl 4-hydroxy-benzoate (102.2 g, 0.61 mol) in AcOH (200 mL) at 65° C. Add dropwise a solution of ICl (100 g, 0.61 moles) in AcOH (500 mL). After the addition, stir the mixture at 65° C. for 6 hours. Pour the mixture into ice/water, filter and wash the solid with water. Dissolve the solid in $CH_2Cl_2$, dry it over $MgSO_4$, filter and concentrate under reduced pressure. Subject residue to silica gel chromatography eluting with $CH_2Cl_2$ to obtain 131.3 g of ethyl 4-hydroxy-3-iodo-benzoate (74% yield).
MS(ES): m/z=291.1 [M-H].

Preparation 2

Ethyl 4-hydroxy-3-cyano-benzoate

Dissolve ethyl 4-hydroxy-3-iodo-benzoate (45 g, 154.1 mmoles) in DMSO (125 mL). Add CuCN (15.17 g, 169.5 mmoles). Stir the mixture at 100° C. overnight. After cooling, pour the mixture into ice/water. Filter the solid obtained, wash with water and dry under reduced pressure. Dissolve the solid in EtOAc. Filter through Celite®. Dry over $MgSO_4$ and remove the solvent to obtain 22.36 g of ethyl 3-cyano-4-hydroxy-benzoate (76% yield). MS(ES): m/z=190.0 [M-H].

Preparation 3

Ethyl 3-cyano-4-trifluoromethanesulfonyloxy-benzoate

Dissolve the ethyl 3-cyano-4-hydroxy-benzoate (22.36 g, 117.1 mmoles) in anhydrous $CH_2Cl_2$ (400 mL) at 0° C. Add $Et_3N$ (24.3 mL, 175.6 mmoles), DMAP (2.14 g, 17.5 mmol), and dropwise $Tf_2O$ (49.5 g, 175.6 mmoles). Stir the mixture at room temperature for 2 hours. Concentrate the mixture under reduced pressure and subject residue to silica gel chromatography eluting hexane/EtOAc 4:1, to obtain 34.99 g of ethyl 3-cyano-4-trifluoromethanesulfonyloxy-benzoate (92% yield). MS(ES): m/z=190.0 [M-H].

Preparation 4

2-Phenyl-1-propylamine HCl

Charge to an autoclave hydrogenation apparatus under nitrogen water-wet 5% palladium on carbon (453 g), ethanol (6.36 L), 2-phenylpropionitrile (636 g, 4.85 moles) and finally concentrated (12M) hydrochloric acid (613 g, 5.6 mole). Stir the mixture rapidly and pressurize to 75 to 78 psi with hydrogen. Heat the mixture 50° C. to 64° C. for 3 hours. Depressurize and filter the reaction mixture to afford two lots of filtrate. Concentrate filtrates under reduced pressure to approximately 400 mL each. Add methyl tert-butyl ether (MTBE) (2.2 L each) to each lot. Stir the precipitate overnight. Filter and wash solids with fresh MTBE (100 mL) and dry overnight. Combine the lots to afford 2-phenyl-1-propylamine HCl (634.4 g, 76.2%) as a white powder.

1H NMR analysis of the free base: 1H NMR (CDCl3, 300 MHz) δ 7.32 (m, 2H), 7.21 (m, 3H), 2.86 (m, 2H), 2.75 (m, 1H), 1.25 (d, 3H, J=6.9), 1.02 (br s, 2H).

Preparation 5

(2R)-2-phenylpropylamine malate

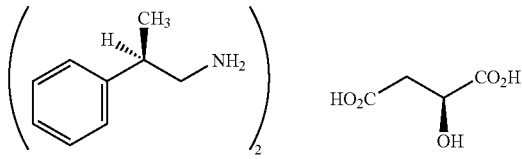

Charge 2-phenyl-1-propylamine HCl (317.2 g, 1.85 moles), dry ethanol (2.0 L) and NaOH beads (75.4 g, 1.89 moles) washed with additional ethanol (500 mL) to a dry 3-L round bottom flask under nitrogen. Stir the mixture for 1.6 hours. Filter and add a solution of L-malic acid (62.0 g, 0.462 mole, 0.25 equivalents) in ethanol (320 mL) dropwise to the yellow filtrate. Heat the solution to 75° C., then stir at 75° C. for 30 minutes. Remove heat and allow the solution to cool slowly. Allow the resulting thick precipitate to stir overnight. Filter the precipitate, rinse with ethanol (325 mL) and dry under reduced pressure to afford (2R)-2-phenylpropylamine malate (147.6 g, 39.5%) as a white crystalline solid. Chiral GC analysis of the free base, 2-phenyl-1-propylamine reveals 83.2% e.e. enriched in the R-isomer. (Configuration is assigned via spectrometric comparison with commercial 2-phenyl-1-propylamine.) 1H NMR (CDCl3, 300 MHz) δ 7.32 (m, 2H), 7.21 (m, 3H), 2.86 (m, 2H), 2.75 (m, 1H), 1.25 (d, 3H, J=6.9), 1.02 (br s, 2H).

Heat a slurry of (2R)-2-phenylpropylamine malate (147.1 g, 83.2% e.e.) in 1325 mL ethanol and 150 mL deionized water to reflux (approximately 79.2° C.) until the solids dissolve. Allow the homogeneous solution to slowly cool with stirring overnight. Cool the precipitate (0° C. to 5° C.) and filter. Collect solids, rinse with ethanol (150 mL), and dry at 35° C. to afford (2R)-2-phenylpropylamine malate (125.3 g, 85.2% recovery) as a white powder. Chiral GC analysis of the free base, (2R)-2-phenylpropylamine, reveals 96.7% e.e. enriched in the R-isomer. 1H NMR (CD3OD, 300 MHz) δ 7.32 (m, 10H), 4.26 (dd, 1H, J=3.6, 9.9), 3.08 (m, 6H), 2.72 (dd, 1H, J=9.3, 15.3), 2.38 (dd, 1H, J=9.3, 15.6), 1.33 (d, 6H, J=6.6).

Preparation 6

Preparation of ((2R)-2-phenylpropyl)[(methylethyl)sulfonyl]amine

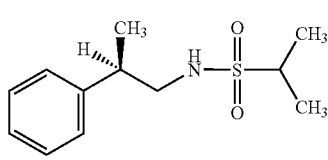

Add 1.0 N NaOH (1050 mL, 1.05 moles) to a stirred slurry of (2R)-2-phenylpropylamine malate (200 g, 0.494 moles) in CH2Cl2 (1000 mL). Stir the mixture at room temperature for 1 hour. Separate the organic phase and gravity filter into a 3.0 L round-bottom flask with a CH2Cl2 rinse (200 mL). Dry the resulting free base, (2R)-2-phenylpropylamine via azeotropic distillation. Concentrate the clear filtrate to a volume of 600 mL at atmospheric pressure via distillation through a simple distillation head. Add heptane (1000 mL), then concentrate the solution again at atmospheric pressure to 600 mL using a nitrogen purge to increase the rate of distillation, with a final pot temperature of 109° C.

Cool the solution to room temperature under nitrogen with stirring to give a clear, colorless heptane solution (600 mL) of (2R)-2-phenylpropylamine. To this solution add 4-dimethylaminopyridine (6.04 g, 0.0494 moles), triethylamine (200 g, 1.98 moles), and CH2Cl2 (500 mL). Stir the mixture at room temperature until a clear solution is obtained. Cool the solution to 5° C. While stirring, add a solution of isopropylsulfonyl chloride (148 g, 1.04 moles) in CH2Cl2 (250 mL) dropwise over 2 hours. Allow the mixture to warm gradually to room temperature over 16 hours.

Cool the stirred mixture to 8° C., then add 2 N HCl (500 mL) dropwise. Separate the organic phase and extract with water (1×500 mL) and saturated NaHCO3 (1×500 mL). Isolate the organic phase, dry with (Na2SO4), and gravity filter. Concentrate the filtrate under reduced pressure to provide ((2R)-2-phenylpropyl)[(methylethyl)sulfonyl]amine (230 g, 96%) as a pale yellow oil. 1H NMR (CDCl3, 300 MHz) δ 7.34 (m, 2H), 7.23 (m, 3H), 3.89 (br t, 1H, J=5.4), 3.36 (m, 1H), 3.22 (m, 1H), 3.05 (m, 1H), 2.98 (m, 1H), 1.30 (d, 3H, J=7.2), 1.29 (d, 3H, J=6.9), 1.25 (d, 3H, J=6.9).

Preparation 7

[(2R)-2-(4-iodophenyl)propyl][(methylethyl)sulfonyl]amine

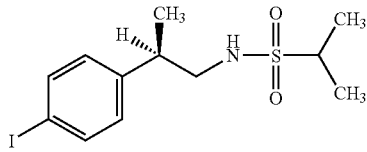

Treat a stirred room temperature solution of ((2R)-2-phenylpropyl)[(methylethyl)sulfonyl]amine (37.1 g, 0.154 moles) in glacial acetic acid (185 mL) with concentrated H2SO4 (16.0 g, 0.163 moles), added dropwise in a slow stream, followed by a H2O rinse (37 mL). Add H5IO6 (8.29 g, 0.0369 moles), followed by iodine (17.9 g, 0.0707 moles) to this solution. Heat the resulting reaction mixture and allow it to stir for 3 hours at 60° C. Analyze starting material consumption by HPLC analysis, then cool the reaction mixture to 30° C. Add a 10% aqueous solution of NaHSO3 (220 mL) dropwise while maintaining the temperature between 25° C. and 30° C. Cool to 0° C. to 5° C. to obtain solids.

Suction filter solids and rinse with H2O to afford 61.7 g of crude solids. Redissolve solids into warm MTBE (500 mL). Extract this solution with H2O (2×200 mL) and saturated NaHCO3 (1×200 mL). Isolate and dry the organic phase with MgSO4, filter, and concentrate under reduced pressure to a volume of approximately 200 mL. Add heptane (100 mL) dropwise to the product solution with slow stirring until crystallization begins. Add an additional 100 mL of heptane.

Allow the resulting suspension to stir slowly overnight at room temperature. Cool the mixture to 0° C. and filter. Rinse the collected solids with heptane. Air-dry the solids to afford [(2R)-2-(4-iodophenyl)propyl][(methylethyl)sulfonyl]amine (33.7 g, 59.8%) as a white powder. Chiral Chromatography indicates 100% e.e.

$^1$H NMR (CDCl$_3$, 300 MHz) δ 7.66 (d, 2H, J=8.1), 6.98 (d, 2H, J=8.4), 3.86 (br t, 1H, J=5.1), 3.33 (m, 1H), 3.18 (m, 1H), 3.06 (m, 1H), 2.92 (m, 1H), 1.30 (d, 3H, J=6.6), 1.27 (d, 6H, J=6.6).

Preparation 8

(2R)-Propane-2-sulfonic acid {2-[4-(4,4,5,5-tetramethyl-[1,3,2]dioxaborolan-2-yl)-phenyl]-propyl}-amide

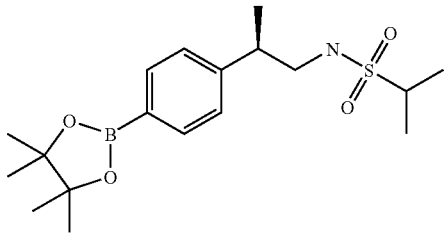

Combine [(2R)-2-(4-Iodophenyl)propyl][(methylethyl)sulfonyl]amine (0.787 g, 2.14 mmol) bis(pinacolate) diboron (0.599 g, 2.36 mmoles), PdCl$_2$ (dppf), CH$_2$Cl$_2$ (0.052 g, 0.064 mmol) and KOAc (0.630 g, 6.42 mmol) in DMF (40 mL) and heat at 80° C. under nitrogen for 10 hours. Pour the resultant dark brown mixture into a EtOAc and wash with H$_2$O and saturated aq. sodium chloride solution. Isolate and dry the organic layer with (MgSO$_4$). Filter and evaporate the filtrate, then subject residue to chromatographic elution to provide the title compound (1.0 g, 78%) as a white solid.

Analysis: Theory: C, 58.86; H, 8.23; N, 3.81. Found: C, 58.84; H, 8.25; N, 3.96.

EXAMPLES

Example 1

1-(R)-2-Cyano-4'-[1-methyl-2-(propane-2-sulfonylamino)-ethyl]-biphenyl-4-carboxylic acid

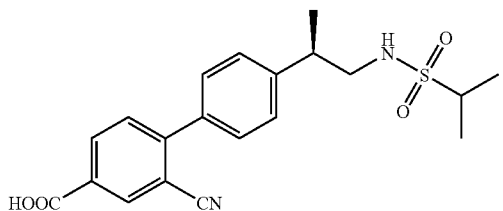

Stir a solution of (2R)-propane-2-sulfonic acid {2-[4-(4,4,5,5-tetramethyl-[1,3,2]dioxaborolan-2-yl)-phenyl]-propyl}-amide (50 g, 136.2 mmol), Ethyl 3-Cyano-4-trifluoromethanesulfonyloxy-benzoate (40 g, 123.8 mmol), PdCl2 (dppf).DCM (3.03 g, 3.71 mmol) and KOAc (36.43 g, 371.4 mmol) in DME:EtOH:H2O (200 mL/200 mL/200 mL) under nitrogen at 80° C. for 50 minutes. Pour the reaction mixture into ice-water and extract it with EtOAc. Wash the organic layer with water and saturated aq. sodium chloride solution, dry over MgSO4, filter and concentrate it in vacuo. Subject residue to silica gel chromatography eluting with hexane/EtOAc 4:1 to 3:1. Triturate the product in hexane, filter and dry, to yield 37.95 g of 1-(S)-Ethyl 2-Cyano-4'-[1-methyl-2-(propane-2-sulfonylamino)-ethyl]-biphenyl-4-carboxylate (74%). MS(ES): m/z=413.1 [M-H].

Stir 1-(R)-ethyl 2-cyano-4'-[1-methyl-2-(propane-2-sulfonylamino)-ethyl]-biphenyl-4-carboxylate (37.95 g, 91.7 mmoles) in EtOH and aqueous NaOH 2N (458 mL, 916 mmoles) at room temperature for 3 hours. Remove the EtOH and wash the aqueous with Et$_2$O. Acidify the aqueous layer using HCl 1N and then extract it with EtOAc. Wash the organic layer with water and saturated aq. sodium chloride solution, dry over MgSO$_4$, filter and concentrate it in vacuo. Triturate the solid in hexane: MTBE 9:1, to yield 28.4 g of 1-(R)-2-Cyano-4'-[1-methyl-2-(propane-2-sulfonylamino)-ethyl]-biphenyl-4-carboxylic acid (80%).

MS(ES): m/z=385.1 [M-H].

The ability of the compound of Formula I to potentiate glutamate receptor-mediated response can be determined by one of ordinary skill in the art. For example, see U.S. Pat. No. 6,303,816. In particular, the following test may be utilized:

HEK293 cells stably expressing human iGluR4 (obtained as described in European Patent Application Publication No. EP-A1-0583917) are used in the electrophysiological characterization of AMPA receptor potentiators. The extracellular recording solution contains (in mM): 140 NaCl, 5 KCl, 10 HEPES, 1 MgCl$_2$, 2 CaCl$_2$, 10 glucose, pH=7.4 with NaOH, 295 mOsm kg-1. The intracellular recording solution contains (in mM): 140 CsCl, 1 MgCl$_2$, 10 HEPES, (N-[2-hydroxyethyl]piperazine-N1-[2-ethanesulfonic acid]) 10 EGTA (ethylene-bis(oxyethylene-nitrilo)tetraacetic acid), pH=7.2 with CsOH, 295 mOsm kg-1. With these solutions, recording pipettes have a resistance of 2-3 MΩ. Using the whole-cell voltage clamp technique (Hamill et al. (1981) Pflügers Arch., 391: 85-100), cells are voltage-clamped at −60 mV and control current responses to 1 mM glutamate are evoked. Responses to 1 mM glutamate are then determined in the presence of test compound. Compounds are deemed active in this test if, at a test concentration of 10 μM or less, they produce a greater than 10% increase in the value of the current evoked by 1 mM glutamate.

In order to determine the potency of the test compound, the concentration of the test compound, both in the bathing solution and co-applied with glutamate, is increased in half log units until the maximum effect is seen. Data collected in this manner are fit to the Hill equation, yielding an EC$_{50}$ value, indicative of the potency of the test compound. Reversibility of test compound activity is determined by assessing control glutamate 1 mM responses. Once the control responses to the glutamate challenge are re-established, the potentiation of these responses by 100 μM cyclothiazide is determined by its inclusion in both the bathing solution and the glutamate-containing solution. In this manner, the efficacy of the test compound relative to that of cyclothiazide can be determined.

The compound described in Example 1 was tested essentially as described above and found to have an activity of 187.8±15.3 nM. As such, the compound described in Example 1 is a potent AMPA potentiator.

In addition, certain behavioral despair animal models, which can be practiced by one of ordinary skill in the art to evaluate compounds of the present invention, are predictive of antidepressant activity in man, such as the Forced Swim Test and the Tail Suspension Test. For example, see "Experimental Approaches to Anxiety and Depression", Edited by J. M. Elliott, et al., (1992), John Wiley & Sons Ltd., Chapter 5, Behavioural Models of Depression, Porsolt and Lenegre, pages 73-85.

Pharmaceutical compositions of the present invention are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 0.1 mg to about 300 mg, preferably about 0.1 mg to about 100 mg, and most preferably about 1.0 to about 100 mg of compound of Formula I. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient.

As used herein the term "patient" refers to a mammal, such as a mouse, guinea pig, rat, dog or human. It is understood that the preferred patient is a human. As used herein, the terms "treating" or "to treat" or "treatment" each mean to alleviate symptoms, eliminate the causation either on a temporary or permanent basis, or to prevent or slow the appearance of symptoms of the named disorder. As such, the methods of this invention encompass both therapeutic and prophylactic administration.

As used herein, the term "effective amount" refers to the amount of a compound of Formula I which is effective, upon single or multiple dose administration to a patient, in treating the patient suffering from the named disorder.

An effective amount can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compound of Formula I can be administered by a variety of routes including oral, rectal, transdermal, subcutaneous, intravenous, intramuscular, bucal or intranasal routes. Alternatively, the compound of Formula I may be administered by continuous infusion. A typical daily dose will contain from about 0.005 mg/kg to about 10 mg/kg of the compound of Formula I. Preferably, daily doses will be about 0.005 mg/kg to about 5 mg/kg, more preferably from about 0.005 mg/kg to about 2 mg/kg.

The dosages of the drugs used in the combinations set forth herein, must also, in the final analysis, be set by the physician in charge of the case, using knowledge of the drugs, the properties of the drugs in combination as determined in clinical trials, and the characteristics of the patient, including diseases other than that for which the physician is treating the patient.

The inert ingredients and manner of formulation of the adjunctive pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compounds, however, is best defined as the effective amount, that is, the amount of each compound which provides the desired dose to the patient in need of such treatment.

For example, a formulation may include 1% carboxymethylcellulose sodium, 0.25% polysorbate 80 and 0.05% Dow Corning® Antifoam 1510-US in purified water) through the oral route. For the IV administration, a number of formulations may be used, such as a composition of 5% Pharmasolve, 1.8% 1N NaOH, 93.2% of 5% dextrose in water or a composition of 5% Pharmasolve, 2:1 molar ratio of NaOH:active ingredient in 5% dextrose.

I claim:

1. A compound of the formula:

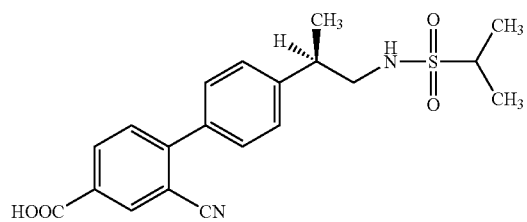

or a pharmaceutically acceptable salt thereof.

2. A pharmaceutical formulation comprising a compound of the formula:

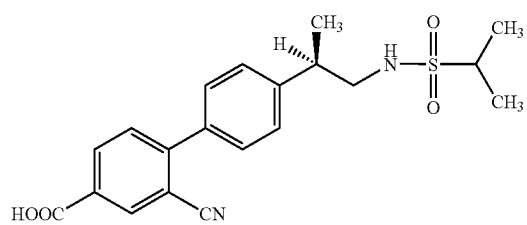

or a pharmaceutically acceptable salt thereof in combination with a pharmaceutically acceptable carrier, diluent or excipient.

3. The compound of claim 1 for use as a pharmaceutical.

4. A method of potentiating glutamate receptor function in a mammal comprising administering to a mammal in need of such treatment an effective amount of a compound of claim 1.

5. A method of treating Parkinson's disease comprising administering to a mammal in need of such treatment an effective amount of a compound of claim 1.

6. A method of treating depression comprising administering to a mammal in need of such treatment an effective amount of a compound of claim 1.

7. A method of treating schizophrenia comprising administering to a mammal in need of such treatment an effective amount of a compound of claim 1.

\* \* \* \* \*